United States Patent [19]
Kohn

[11] Patent Number: 5,880,158
[45] Date of Patent: Mar. 9, 1999

[54] PROPIONAMIDE ANTICONVULSANTS

[75] Inventor: Harold Kohn, Houston, Tex.

[73] Assignee: Research Corporation Tech., Inc., Tucson, Ariz.

[21] Appl. No.: 938,527

[22] Filed: Sep. 26, 1997

Related U.S. Application Data

[60] Provisional application No. 60/026,847 Sep. 27, 1996.
[51] Int. Cl.$^6$ .......................... A61K 31/16; C07C 233/05
[52] U.S. Cl. .......................... 514/625; 514/617; 514/618; 514/619; 514/620; 514/626; 564/193; 564/194; 564/196; 564/201; 564/202; 564/203; 564/223
[58] Field of Search ..................................... 564/193, 194, 564/196, 201, 202, 203, 223; 514/617, 618, 619, 620, 626, 625

[56] References Cited

U.S. PATENT DOCUMENTS 5,378,729 1/1995 Kohn et al. ........................ 514/231.2

OTHER PUBLICATIONS

Choi, et al. "Synthesis and Anticonvulsant Activities of N–Benzyl–2–acetamidopropionamide Derivatives", J. Med. Chem., vol. 39, pp. 1907–1916, 1996.

Choi, et al. "The Anticonvulsant Activities of Functionalized N–Benzyl 2–Acetamidoacetamides", Bioorganic and Medicinal Chemistry, vol. 4, pp. 2105–2114, 1996.

*Primary Examiner*—Shailendra Kumar
*Attorney, Agent, or Firm*—Scully, Scott, Murphy & Presser

[57] ABSTRACT

The present invention is directed to a compound of the following formula:

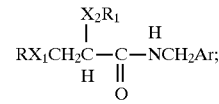

pharmaceutical compositions containing the same and the use thereof as an anticonvulsant.

33 Claims, No Drawings

PROPIONAMIDE ANTICONVULSANTS

CROSS REFERENCE TO RELATED APPLICATION

This application claims the benefit of U.S. Provisional Application No. 60/026,847, filed Sep. 27, 1996.

FIELD OF THE INVENTION

The present invention relates to novel compounds useful as anticonvulsants.

BACKGROUND OF THE INVENTION

The predominant application of anticonvulsant drugs is the control and prevention of seizures associated with epilepsy or related central nervous system disorders. Epilepsy refers to many types of recurrent seizures produced by paroxysmal excessive neuronal discharges in the brain; the two main generalized seizures are petit mal, which is associated with myoclonic jerks, akinetic seizures, transient loss of consciousness, but without convulsion; and grand mal which manifests in a continuous series of seizures and convulsions with loss of consciousness.

The mainstay of treatment for such disorders has been long-term and consistent administration of anticonvulsant drugs. Most drugs in use presumably exert their action on neurons, glial cells or both of the central nervous system. The majority of these compounds are characterized by the presence of at least one amide unit and one or more benzene rings that are present as a phenyl group or as part of a cyclic system.

Much attention has been focused upon the development of anticonvulsant drugs. As a result many such drugs have been prepared. For example, the hydantoins, such as phenytoin, are useful in the control of generalized seizures and all forms of partial seizures. The oxazolidinediones, such as trimethadione and paramethadione, are used in the treatment of nonconvulsive seizures. Phenacemide, a phenylacetylurea, is one of the anticonvulsants employed today. However recently, much attention has been focused on diazepines and piperazines. For example, U.S. Pat. Nos. 4,002,764 and 4,178,378 to Allgeier, et al. disclose esterified diazepine derivatives useful in the treatment of epilepsy and other nervous disorders. U.S. Pat. No. 3,887,543 to Nakanishi, et al. describes a thieno [2,3-e] [1,4] diazepine compound also having anticonvulsant activity and other depressant activity. U.S. Pat. No. 4,209,516 to Heckendorn, et al. relates to triazole derivatives which exhibit anticonvulsant activity and are useful in the treatment of epilepsy and conditions of tension and agitation. U.S. Pat. No. 4,372,974 to Fish, et al. discloses a pharmaceutical formulation containing an aliphatic amino acid compound in which the carboxylic acid and primary amine are separated by three or four units. Administration of these compounds in an acid pH range is useful in the treatment of convulsion disorders and also possess anxiolytic and sedative properties.

U.S. Pat. No. 5,378,729 to Kohn, et al. discloses compounds and pharmaceutical compositions having central nervous system (CNS) activity which are useful in the treatment of epilepsy and other CNS disorders having the formula:

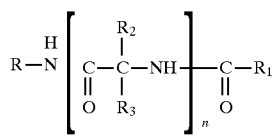

wherein
R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or substituted with at least one election withdrawing group or election donating group;

$R_1$ is hydrogen, lower alkyl, lower alkenyl, lower alkynyl, aryl lower alkyl, aryl, heterocyclic lower alkyl, heterocyclic, lower cycloaklyl, lower cycloalkyl lower alkyl, each unsubstituted or substituted with an electron donating group or an electron withdrawing group;

$R_2$ and $R_3$ are independently hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, or Z-Y, wherein $R_2$ and $R_3$ may be unsubstituted or substituted with at least one electron withdrawing group or electron donating group:

Z is O, S, S $(O)_a$, $NR_4$, $PR_4$ or chemical bond;

Y is hydrogen, lower alkyl, aryl, aryl lower alkyl, lower alkenyl, lower alkynyl, halo, heterocyclic or heterocyclic lower alkyl, and Y may be unsubstituted or substituted with an electron donating group or an electron withdrawing group, provided that when Y is halo, Z is a chemical bond; or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_7$, $PR_4SR_7$, $NR_4PR_5R_6$, $$PR_4NR_5R_7, \quad NR_4\underset{\underset{O}{\|}}{C}R_5, \quad \underset{\underset{O}{\|}}{S}CR_5, \quad NR_4\underset{\underset{O}{\|}}{C}OR_5, \quad \text{or} \quad \underset{\underset{O}{\|}}{S}C-OR_5;$$

$R_4$, $R_5$ and $R_6$ are independently hydrogen, lower alkyl, aryl, aryl lower alkyl, lower alkenyl, or lower alkynyl, wherein $R_4$, $R_5$, and $R_6$ may be unsubstituted or substituted with an electron withdrawing group or an electron donating group;

$R_7$ is $R_6$, $COOR_8$ or $COR_8$;

$R_8$ is hydrogen, lower alkyl or aryl lower alkyl and the aryl or alkyl group may be unsubtituted or substituted with an electron withdrawing group or an electron donating group;

n is 1–4 and a is 1–3.

Unfortunately, despite the many available pharmacotherapeutic agents for the treatment of epilepsy, a significant percentage of the population with epilepsy still suffers from this malady. Moreover, none of the drugs presently available are capable of achieving total seizure control and most have disturbing side effects. Clearly, current therapy has failed to fully control these debilitating diseases.

These shortcomings of these drugs on the market has prompted the present inventor to find new drugs having anticonvulsant properties. The present invention provides novel compounds exhibiting CNS activity, particularly anticonvulsant activity, which are useful for treating epilepsy and other CNS disorders.

SUMMARY OF THE INVENTION

Accordingly, the present invention is directed to propionamides of the formula:

$$\underset{\underset{H}{|}}{RX_1CH_2C} - \underset{\underset{O}{\|}}{\overset{\overset{X_2R_1}{|}}{C}} - NCH_2Ar \qquad \text{I}$$

or pharmaceutically acceptable salts thereof wherein

Ar is aryl which is unsubstituted or substituted with at least one electron donating group or electron withdrawing group;

R and $R_1$ are independently lower alkyl, aryl, aryl lower alkyl, lower cycloalkyl or lower cycloalkyl lower alkyl, wherein R and $R_1$ groups are independently unsubstituted or substituted with at least one electron donating group or electron withdrawing group;

$X_1$ and $X_2$ are independently O, S or $NR_3$; and $R_3$ is hydrogen or lower alkyl.

The present invention is also directed to pharmaceutical compositions containing pharmaceutically effective amounts of the propionamides of the present invention. In addition, the present invention is also directed to a method of treating central nervous system disorders in animals, especially mammals, in need of such treatment comprising administering thereto an anticonvulsant effective amount of the propionamide of the present invention. The administration of an effective amount of the present compounds in their pharmaceutically acceptable form provides an excellent regime for the treatment of epilepsy, nervous anxiety, psychosis, insomnia, and other central nervous disorders.

DETAILED DESCRIPTION OF THE PRESENT INVENTION

As used herein, the term "lower alkyl", when used alone or in combination with other groups, refers to alkyl groups containing 1–6 carbon atoms, which may be straight-chained or branched. These groups include methyl, ethyl, propyl, isopropyl, butyl, isobutyl, tertiary butyl, sec-butyl, amyl, pentyl, isopentyl, hexyl, and the like. The preferred alkyl group is methyl.

The term "aryl", when used alone or in combination with other groups, refers to an aromatic group which contains no heteroatoms and which contains from 6 up to 18 ring carbon atoms and up to a total of 25 carbon atoms. The aryl group may be monocyclic, bicyclic, or tricyclic. If more than 1 ring is present, the rings are fused. The aryl groups also include polynuclear aromatics. By polynuclear aromatics, it is meant to encompass bicyclic and tricyclic fused aromatic ring systems containing from 10–18 ring carbon atoms and up to a total of 25 carbon atoms. Examples of aryl include phenyl, naphthyl (both $\alpha$ and $\beta$), anthracenyl, phenanthrenyl, azulenyl, and the like. The preferred aryl group is phenyl.

The "aryl lower alkyl" group refers to a lower alkyl group, as defined herein, bridging an aryl group, as defined herein, to the main chain. Examples include benzyl, phenethyl, phenpropyl, phenisopropyl, phenbutyl, diphenylmethyl, 1,1-diphenylethyl, 1,2-diphenylethyl, and the like.

The term "lower cycloalkyl" when used alone or in combination with other groups is a cycloalkyl group containing 3–6 ring carbon atoms and up to total of 10 carbon atoms. The cycloalkyl group is monocyclic and is completely saturated. Examples include cyclopropyl, cyclobutyl, cyclopentyl and cyclohexyl and the like. Substituted cycloalkyl groups include both the cis and trans forms.

"Lower cycloalkyl lower alkyl" when used herein denotes a lower alkyl group, as defined herein, bridging a lower cycloalkyl group as defined herein to the main chain. Examples include cyclopropylmethyl, cyclopentylmethyl, cyclohexylmethyl, cyclobutylpropyl, cyclohexylmethyl, cyclobutylmethyl, and the like.

The terms "electron withdrawing groups" and "electron donating groups" refer to the ability of a substituent to withdraw or donate electrons relative to that of hydrogen if the hydrogen atom occupied the same position in the molecule. These terms are well understood by one skilled in the art and are discussed in *Advanced Organic Chemistry*, by J. March, 4th Ed. John Wiley and Sons, New York, N.Y. pp 16–18 (1992), and the discussion therein is incorporated by reference. Examples of electron withdrawing groups include halo, especially fluoro, bromo, chloro, iodo, and the like; nitro; carboxy; formyl; lower alkanoyl; carboxyamido; triloweralkylamino; aryl; trifluoromethyl; aryl lower alkanoyl; lower carbalkoxy; and the like. Examples of electron donating groups include such groups as hydroxy; lower alkoxy, including methoxy, ethoxy, and the like; lower alkyl; amino; lower alkylamino; diloweralkylamino; aryloxy (such as phenoxy); mercapto; mercapto lower alkyl; disulfide; lower alkylthio; and the like. One skilled in the art will appreciate that the aforesaid substituents may have electron donating properties under one set of circumstances and electron withdrawing properties under different chemical conditions or circumstances; these are also contemplated to be within the scope of these terms. Moreover, the present invention contemplates any combination of substituents selected from the above-identified terms.

The term "lower alkanoyl" refers to a lower alkyl group in which a methylene group is replaced by a carbonyl $$\underset{O}{\overset{(C),}{\|}}$$

or in which a carbonyl group bridges the main chain of formula I with lower alkyl or in which a lower alkyl group bridges a formyl group $$(-\underset{O}{\overset{\|}{C}}-H)$$

to the main chain of Formula I. Examples include acetyl, propionyl, and the like.

"Lower alkoxy" denotes an alkyl group which is bridged to the main chain of Formula I by an O. Examples include methoxy, ethoxy, propoxy, and the like.

"Lower carbalkoxy" refers to a group of the formula $$\underset{C-O-}{\overset{O}{\|}}$$

(lower alkyl), wherein lower alkyl is defined herein above.

It is preferred that $X_1$ is O, S or NH. It is also preferred $X_2$ is O, S or NH. It is more preferred that at least one of $X_1$ and $X_2$ is O or S, and even more preferable that $X_1$ and $X_2$ are independently O or S. It is especially preferred that $X_1$ and $X_2$ are the same. It is even more preferred that one of $X_1$ and $X_2$ is O. It is most preferred that $X_1$ and $X_2$ are both O.

The preferred values of R and $R_1$ are independently lower alkyl. It is most preferred that R and $R_1$ are the same. The most preferred values of R and $R_1$ are methyl.

The preferred value of $R_3$ is methyl and especially hydrogen.

A preferred embodiment of the present invention has the formula:

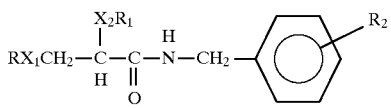

wherein R, $X_1$, $X_2$, and $R_1$ are as defined hereinabove and $R_2$ is hydrogen, an electron withdrawing group or an electron donating group.

It is preferred that $R_2$ is hydrogen, lower alkyl or an electron withdrawing group, especially halo. It is even more preferred that $R_2$ is fluoro and especially hydrogen. The more preferred $X_1$, $X_2$, R and $R_1$ are as described hereinabove.

A more preferred embodiment of the present invention has the formula:

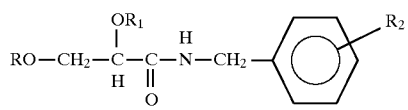

wherein R, $R_1$ and $R_2$ are as defined herein. It is preferred that R and $R_1$ are the same. The more preferred R and $R_1$ groups are lower alkyl. It is most preferred that R and $R_1$ group are both methyl. The preferred values of $R_2$ are as defined hereinabove.

The compounds of the present invention contain at least one asymmetric carbon at the position a to the acyl group

As a result, the compounds of the present invention can exist in at least two stereoisomeric forms around this asymmetric carbon, the R and the S stereoisomer. Both stereoisomers as well as mixtures thereof, including racemic mixtures, are contemplated by the present invention. Additional asymmetric centers may exist in the side chains; the various stereoisomers, and mixtures thereof, including racemic mixtures, are contemplated by the present invention.

It is preferred that the compounds of the present invention be substantially pure, i.e., substantially free from impurities. It is most preferred that the compounds of the present invention be at least 75% pure (w/w) and more preferably greater than 90% pure (w/w) and most preferably greater than about 95% pure (w/w).

In a preferred embodiment of the present invention, the compounds of the present invention are enantiomerically pure, i.e., present in substantially one isomeric form, e.g., substantially the R stereoisomer (or the corresponding S stereoisomer) around the asymmetric carbon that is alpha to the acyl group in the compound of Formula I.

It is to be understood that all combinations and permutations of the various Markush groups for the different variables are contemplated by the present invention. In addition, the various stereoisomers generated therefrom is also contemplated to be within the scope of the present invention.

The compounds of the present invention are prepared by art recognized techniques from commercially available starting materials. Exemplary procedure for making the compounds of the present invention are outlined hereinbelow. When $X_1$ and $X_2$ are both O and R and $R_1$ are both the same, the following scheme is exemplary:

SCHEME 1

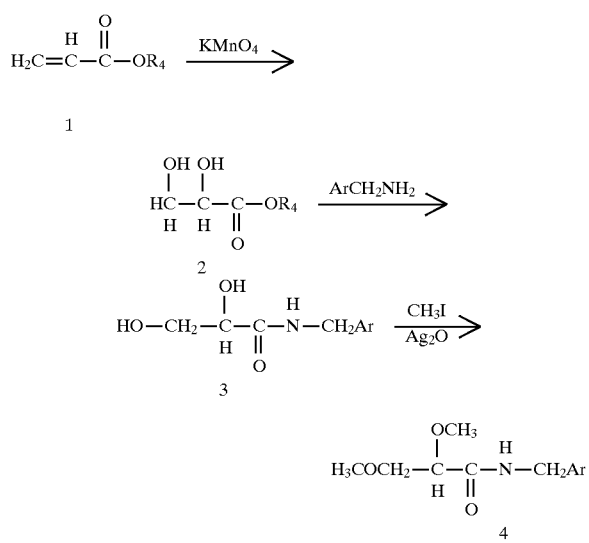

wherein
R = $R_1$
$R_4$ = lower alkyl, such as ethyl, methyl; or arylalkyl, such as benzyl.

Hydroxylation of an ester of acrylic acid (1) using oxidizing agents known in the art, such as alkaline $KMnO_4$, $OsO_4$, and the like, provides the diol (2). The product 2 next undergoes an acylation reaction with $ArCH_2NH_2$ to form the corresponding amide (3). The product 3 is converted to the diether (4) under Williamson reaction conditions, i.e., 3 is reacted with RX, wherein R is as defined herein, such as methyl and X is a good leaving group, such as OTs, OMs, halide or the like in the presence of base e.g., ($Ag_2O$) to form the product 4.

Another more general procedure is as follows:

SCHEME 2

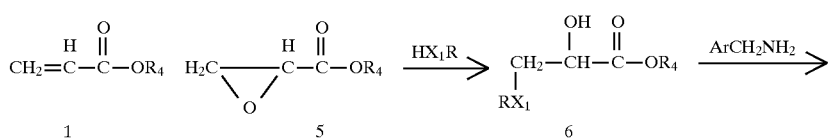

-continued
SCHEME 2

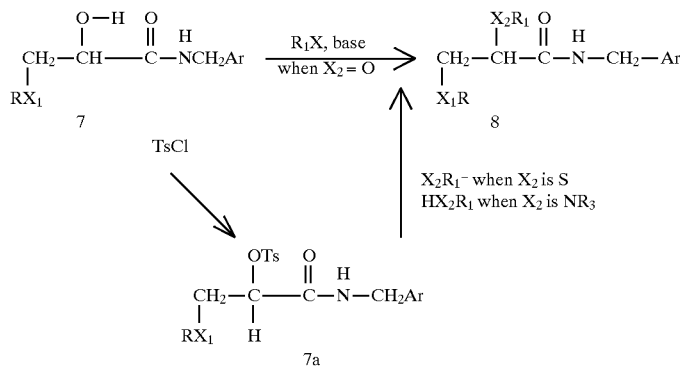

(5) is prepared by art recognized techniques. The epoxide (5) is formed by reacting 1 (the ester of acrylic acid) with a peracid such as m-chloroperbenxoic acid, under Prilezhaev conditions. Other peracids, such as peracetic acid, perbenzoic acid, trifluoroperacetic acid, 3, 5-dinitroperoxybenzoic acid may also be utilized.

The epoxide (5) is reacted with $HX_1R$ under basic or neutral conditions; under these conditions the ring opens up with the less substituted carbon being attacked by the reagent $HX_1R$ to form the product (6). The product (6) is then reacted with $ArCH_2NH_2$ under amide forming conditions to form the amide (7). To form the ether (8), the amide (7) is reacted with $R_1X$, where X is a good leaving group, such as mesylate, tosylate or halide in the presence of base under Williamson reaction conditions. However, if $X_2$ is S or $NR_3$, it is preferable to first convert the hydroxy group to a more reactive intermediate, such as the tosylate or mesylate by reacting 7 with TsCl (or MsCl) to form the corresponding tosylate 7a (or mesylate) which is then reacted with $R_1S^\ominus$ under nucleophilic conditions to form the corresponding thioether or $HNR_1R_3$ under alkylation conditions to form the corresponding amine.

In a variation thereof, amide formation may proceed the epoxide opening as follows:

SCHEME 2A

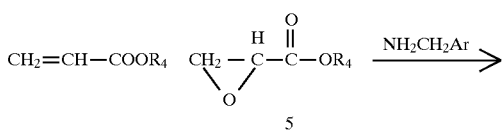

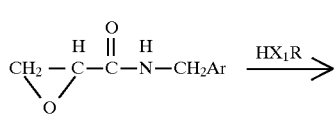

-continued
SCHEME 2A

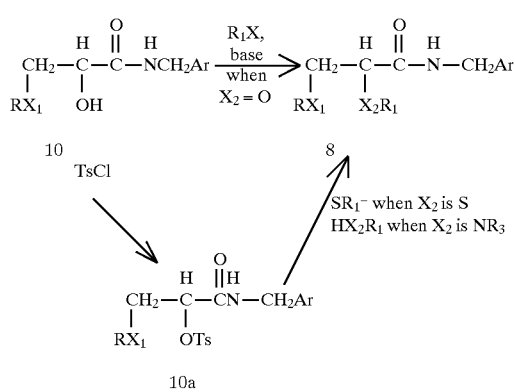

In this variation, the epoxide (5) is formed from acrylic acid ester by reacting it with a peracid such as that described hereinabove. Then 5 is reacted with $NH_2CH_2Ar$ under amide forming conditions to form the corresponding amide (9). 9 is then reacted with $H_1XR$ under neutral or basic conditions to form 10, which is then converted to 8 under the conditions discussed hereinabove in Scheme 2.

In another variation, the amide is formed last as indicated hereinbelow:

SCHEME 2B

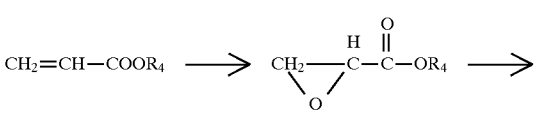

-continued
SCHEME 2B

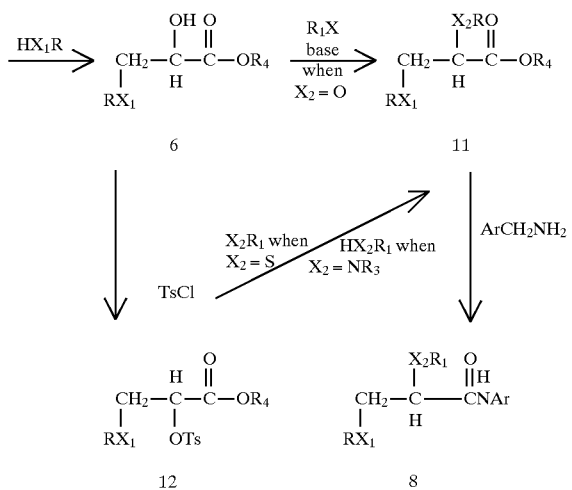

The ester of acrylic acid is converted to the corresponding epoxide, which is then reacted with $HX_1R$ as in Scheme 2 to form the corresponding alcohol 6. 6 is then converted to 11 by reacting it with alkyl halide and base under Williamson reaction conditions to form the corresponding ether. Alternatively, the OH group in 6 is converted to a more reactive group, such as by reacting 6 with mesyl chloride or tosyl chloride to form 12 and the product 12 is reacted with $X_2R_1^-$ when $X_2$ is S or $HX_2R_1$ when $X_2$ is $NR_3$ under nucleophile reaction conditions or alkylation conditions, respectively to form (11). 11 is reacted with $ArCH_2NH_2$ under amide forming conditions to form 8.

Another variation depicted for $X_1$ and $X_2$ being oxygen is indicated hereinbelow.

SCHEME 3

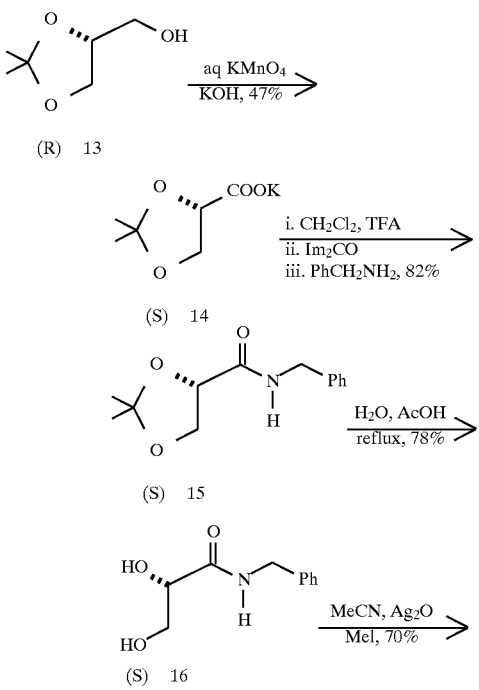

-continued
SCHEME 3

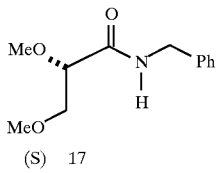

(R)(−)-2,2-dimethyl-1,3-dioxolane-4-methanol, which is commercially available, is oxidized with an oxidizing agent, such as potassium permanganate to form the corresponding acid salt (14). 14 is then reacted with $ArCH_2NH_2$ under amide forming conditions to form the corresponding amide acetal (15). Acid hydrolysis of the acetal (15) forms the corresponding diol 16 which is then reacted with alkyl halide in the presence of base under Williamson reaction conditions to form the corresponding diether.

The enantiomer of 17 is synthesized by starting with S-(+)-2,2-dimethyl-1,3-dioxolane-4-methanol, and following the procedure indicated hereinabove, as shown in Scheme 4.

SCHEME 4

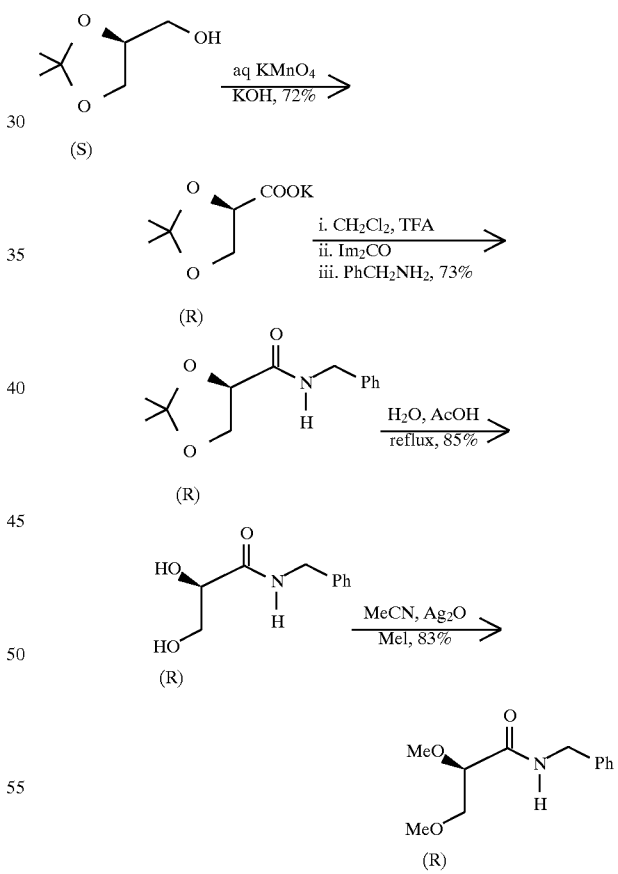

In the above schemes, R, $R_1$, $R_3$, $R_4$, X, $X_1$, $X_2$, and Ar are as defined hereinabove.

The various substituents in the final products, e.g., on R, $R_1$, $R_3$ and Ar may be present in the starting compounds, added to any of the intermediates or added after formation of the final products by known methods of substitution or conversion reactions. For example, the nitro groups can be added to the aromatic ring by nitration, and the nitro groups can be converted to other groups, such as amine by reduction; halo by diazotization of the amino group and then replacement by cuprous halide under Sandmeyer reaction conditions. Alternatively, replacement of the diazonium group by reacting the diazonium salt with fluoroboric acid, $HBF_4$, followed by heating forms the corresponding fluoride. The alkanoyl group can be substituted onto the aryl groups by Friedel Crafts acylation. The alkanoyl groups can then be transformed to the corresponding alkyl groups by various methods, including Wolff-Kishner reduction and Clemmenson reduction. Amino groups can be alkylated to form mono-or dialkylamino groups and mercapto and hydroxy groups can be alkylated to form corresponding thioethers and ethers, respectively. Primary alcohols can be oxidized by oxidizing agents known in the art to form carboxylic acids or aldehydes and secondary alcohols can be oxidized to form ketones. Thus, substitutions or alteration reactions can be employed to provide a variety of substituents throughout the molecule of the starting material, intermediates or the final product.

In the above reactions, if the substituents themselves are reactive, then the substituents can themselves be protected according to the techniques known in the art. A variety of protecting groups known in the art may be employed. Examples of many of these groups may be found in *Protective Groups* in *Organic Syntheses,* by T. W. Greene, John Wiley and Sons, (1981), the contents of which are incorporated by reference.

Resulting mixtures of isomers are separated into purer isomers by methods known to one skilled in the art, e.g., by fractional distillation, crystallization chromatography, combination of these techniques and the like.

The present compounds exist in stereoisomeric forms, and the products obtained thus can be mixtures of the isomers, which are resolved by art recognized techniques. For example, racemic products can be resolved into optical antipodes by fractional crystallization, by the use of chiral stationery phase chromatography (HPLC) and the like. For a discussion of chiral stationary phase for HPLC, See DeCamp, *Chirality,* 1, 2–6 (1989), the contents of which are incorporated herein by reference.

The compounds of the present invention exhibit excellent anticonvulsant activity when administered in amounts ranging from about 0.5 mg to about 100 mg per kilogram of body weight per day. A preferred dosage regimen ranges from about 10 mg per kilogram per day to about 50 mg per kilogram per day. This dosage regime may be adjusted by the physician to provide the optimum therapeutic response. For example, several divided doses may be administered daily or the dose may be proportionally reduced as indicated by the exigencies of the therapeutic situation. A decided practical advantage is that the active compound may be administered in an convenient manner such as by the oral, intravenous (where water-soluble), intramuscular or subcutaneous routes.

The active compound may be orally administered, for example, with an inert diluent or with an assimilable edible carrier, or it may be enclosed in hard or soft shell gelatine capsules, or it may be compressed into tablets, or it may be incorporated directly into the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 5 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitioneally. Dispersions can also be prepared in glycerol, liquid polyethylene glycols, and mixture thereof and in oils. Under ordinary conditions of storage and use, these preparations contain a preservative to prevent the growth of microorganisms.

The pharmaceutical forms suitable for injectable use include sterile aqueous solutions (where water-soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization.

Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parental compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased conditions in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 5 to about 1000 mg. Expressed in proportions, the active compound is generally present in from about 1 to about 750 mg/ml of carrier. In the case of compositions containing supplementary active ingredients, the dosages are determined by reference to the usual dose and manner of administration of the said ingredients.

Unless indicated to the contrary, percentages are by weight.

For a better understanding of the present invention reference is made to the following description and examples.

GENERAL METHODS

Melting points were determined with a Thomas-Hoover melting point apparatus and are uncorrected. Infrared spectra (IR) were run on a ATI Mattson Genesis Series FTIR™ spectrometer. Absorption values are expressed in wavenumbers ($cm^{-1}$). Proton ($^1$H NMR) and carbon ($^{13}$C NMR) nuclear magnetic resonance spectra were taken on a General Electric QE-300 NMR instrument. Chemical shifts (δ) are in parts per million (ppm) relative to tetramethylsilane and couplings constants (J values) are in Hertz. Low resolution mass spectra (CI+) were obtained with a Varian MAT CH-5 spectrometer by Dr. M. Moini at the University of Texas-Austin. The high-resolution chemical ionization mass spectrum was performed on a Finnigan MAT TSQ-70 by Dr. M. Moini at the University of Texas-Austin. Microanalyses were provided by Atlantic Microlab. Inc. (Norcross, Ga.). Thin-layer chromatography was performed on precoated silica gel GHLF microscope slides (2.5×10 cm; Analtech No. 21521).

EXAMPLE 1

PREPARATION OF N-BENZYL 2,3-DIMETHOXY PROPIONAMIDE

A. Ethylglycerate $KMnO_4$(15.65 g, 99 mmol) was dissolved in $H_2O$ (150 mL) and acetone (300 mL) and then cooled to $-78°$ C. Ethyl acrylate (9.75 mL, 90 mmol) was slowly added with stirring at $-78°$ C., and then the reaction mixture was allowed to warm up to $0°$ C. The inorganic salts were removed by filtration and washed with acetone (150 mL). The combined filtrates were concentrated under reduced pressure at temperatures below $40°$ C. The product was extracted using EtOAc (3×200 mL), dried ($Na_2SO_4$), and then the solvent was removed under reduced pressure to afford the above-identified product as a white oil (6.70 g, 56%): $R_f$ 0.60 (30% MeOH-$CHCl_3$); $^1$H NMR ($CDCl_3$) δ 1.32 (t, J=7.2 Hz, $OCH_2OH_3$), 2.31 (br s OH), 3.27 (br s, OH), 3.85 (dd, J=3.0, 11.7 Hz, CHH'OH), 3.91 (dd, J=3.3, 11.7 Hz, CHH'OH), 4.25–4.27 (m, CH), 4.29 (q, J=7.2Hz, $OCH_2CH_3$); $^{13}$C NMR ($CDCl_3$) 13.6 ($OCH_2CH_3$), 61.1 ($OCH_2CH_3$) 63.7 ($CH_2OH$), 71.6 (CHOH), 172.5 (C(O)) ppm.

B. N-Benzyl 2,3-Dihydroxypropionamide

To the product of A (6.71 g, 50 mmol) was added benzylamine (5.74 mL, 100 mmol), and then the reaction solution was stirred at $100°$ C. (18 h). The excess benzylamine was removed in vacuo, and the residue triturated with $CHCl_3$ (100 mL) to solidify the product. The mixture was filtered to give the above product as a white solid (6.30 g, 65%): mp $83°–84°$ C.; $R_f$ 0.37 (10% MeOH-$CHCl_3$); IR (KBr) 3408, 3294, 3033, 2926, 1627, 1531, 1426, 1103, 1067, 730 $cm^{-1}$; $^1$H NMR (DMSO-$d_6$) δ 3.40–3.51 (m, CHH'OH), 3.57–3.63 (m, CHH'OH), 3.89–3.94 (m, CHOH), 4.28 (d, J=6.3 Hz, $CH_2NH$), 4.72 (t, J=5.7 Hz, $CH_2OH$), 5.55 (d, J=5.4 Hz, CHOH), 7.12–7.32 (m, 5PhH), 8.22 (t, J=6.3 Hz, $CH_2NH$); $^{13}$C NMR (DMSO-$d_6$) 41.7 ($CH_2NH$), 63.9 ($CH_2OH$), 73.1 (CHOH), 126.6 ($C_4$'), 127.1 ($2C_2$' or $2C_3$'), 128.1 ($2C_2$' or $2C_3$'), 139.6 ($C_1$'), 172.2 (C(O)) ppm; MS, (CI+) (rel intensity) 196 ($M^+$+1, 100); $M_r$ (+Cl) 196.097 51 [$M^+$+1] (calcd for $C_{10}H_{14}NO_3$ 196.097 37).

Anal Calcd for $C_{10}H_{13}NO_3$: C, 61.57; H, 6.71; N, 7.18. Found: C,61.68; H, 6.76; N, 7.18.

C. N-Benzyl 2,3 -Dimethoxypropionamide $Ag_2O$ (9.27 g, 40 mmol) and MeI (4.98 mL, 80 mmol) were added to room temperature to a stirred acetonitrile solution (50 mL) of the product of B (1.56 g, 8 mmol), and then the reaction mixture was stirred at room temperature (2d). The insoluble salts were filtered, and the solvent was removed in vacuo. The product was purified by flash column chromatography (EtOAc), and then further purified by distillation under reduced pressure ($147°$ C./0.8 Torr) to give the above as a white oil (1.20 g, 67%): $R_f$ 0.67 (5% MeOH-$CHCl_3$); IR (KBr) 3419, 3319, 2931, 1661, 1529 1454, 1131, 1108, 735, 701 $cm^{-1}$; $^1$H NMR ($CDCl_3$) δ 3.40 (br s, $CH_2OCH_3$), 3.48 (br s, $CHOCH_3$), 3.70 (dd, J=4.5, 10.5 Hz, CHH'$OCH_3$), 3.79 (dd, J=2.4, 10.5Hz, CHH'$OCH_3$), 3.87 (dd, J=2.4, 4.5 Hz, CH), 4.50 (d, J=6.0 Hz, $CH_2NH$), 6.98 (br s, $CH_2NH$), 7.25–7.36 (m, 5PhH); $^{13}$C NMR ($CDCl_3$) 42.3 ($CH_2NH$), 58.0 ($CH_2OCH_3$ or $CHOCH_3$), 58.7 ($CH_2OCH_3$ or $CHOCH_3$), 71.8 ($CH_2OCH_3$), 81.3 ($CHOCH_3$), 126.8 ($C_4$'), 126.9 ($2C_2$' or $2C_3$') 128.0 ($2C_2$' or 2C3') 137.7 ($C_1$'), 169.4 (C(O)) ppm; MS, (CI+) (rel intensity) 224 ($M^+$+1, 100); $M_r$ (+CI) 224.128 47 [$M^+$+1] (calcd for $C_{12}H_{18}NO_3$ 224.128 67).

Anal Calcd for $C_{12}H_{17}NO_3$: C, 62:91; H, 7.77; N, 6.11. Found: C, 63.12; H, 7.65; N, 6.09.

EXAMPLE 2

S-N-Benzyl-2,3-Dimethoxypropionamide

A. Postassium (S)-2,2-dimethyl-1,3-dioxolane-4-carboxylate

A solution of (R)-(+)-2,2-dimethyl-1,3-dioxolane-4-methanol (2.00 g, 15 mmol) and KOH (0.90 g, 16 mmol) in $H_2O$ (60 ml) was cooled to 0° C. and $KMnO_4$ (2.52 g, 16 mmol) was incrementally added. Upon addition, the reaction mixture was allowed to warm to room temperature, and then stirred for an additional 2 hours. The mixture was filtered through Celite and the clear filtrate was adjusted to pH 8.0 with 5% aqueous $H_2SO_4$. The resulting solution was evaporated in vacuo, and the white residue was suspended in boiling EtOH (100 ml) and filtered. Evaporation of the solvent gave the desired product as a while solid (1.3 g, 47%): $[\alpha]^{23}D=-28.2°$ (c=0.65, $H_2O$).

B. (S)-N-Benzyl-2,2-dimethyl-1,3-dioxolane-4-carboxamide.

The (S)-N-benzyl-2,d-dimethyl-1,3-dioxolane-4-carboxamide was prepared as follows:

Potassium (S)-2,2-dimethyl-1,3-dioxolane-4-carboxylate (2.86 g, 15.54 mmol) was suspended in dry $CH_2Cl_2$ (50 mL) under $N_2$. Trifluoroacetic acid (1.77 g, 15.54 mmol) was then added, and the reaction stirred at room temperature for about 30 minutes. 1,1'-Carbonyldiimidazole (2.60 g, 16 mmol) was then introduced at room temperature, and the reaction was heated at reflux until $CO_2$ evolution ceased. The reaction mixture was cooled to room temperature and benzylamine (1.81 mL, 16.54 mmol) was added. The reaction was stirred for about 8 hours. The $CH_2CH_2$ suspension was washed with water (2×25 mL) and the organic layer separated, dried ($NaS_2O_4$) and evaporated in vacuo. The residue was purified by silica gel column chromatography (5% MeOH-$CHCl_3$) to obtain the crude amide, which was then further purified by recrystallization from ethyl ether-petroleum ether to obtain 3.00 g (82%) of the desried product: mp 84°–87° C.; $R_f$ 0.70 (5% MeOH-$CHC_3$); $[\alpha]^{23}D=-17.2°$ (c=0.08, MeOH); IR (KBr) 3336, 1649, 1540, 1220, 1090, 735, 502 $cm^{-1}$; $^1H$ NMR ($CDCl_3$) δ 1.39 (s, $CCH_3$), 1.45 (S, $CCH_3$), 4.16 (dd, J=5.4, 9.0 Hz, OCHH'), 4.32 (dd, J=7.6 Hz, OCHH'), 6.80–6.95 (m, NH), 7.20–7.41 (m, PhH); $^{13}C$ NMR ($CDCl_3$) 25.0 ($CCH_3$), 26.2 ($CCH_3$), 42.9 ($CH_2Ph$), 67.8 ($CH_2$), 75.1 (CH), 110.9 ($C(CH_3)_2$), 127.6 ($2C_2'$ or $2C_3'$ and $C_4'$), 128.8 ($2C_2'$ or $2C_3'$), 137.9 ($C_1'$), 171.2 (C(O)) ppm; MS (+Cl) (rel. intensity) 236 ($M^+$+1, 100), 208(7), 178 (20); $M_r$ (+Cl) [$M^+$+1 236.128 44 (calcd for $C_{13}H_{18}NO_3$ 236.128 67); Anal. ($C_{13}H_{17}NO_3$Ω025 $H_2O$) C,H, N.

C. (S)-N-Benzyl-2,3-dihydroxypropionamide.

(S)-N-benzyl-2,3-dihydroxypropionamide was prepared in the following manner: (S)-N-benzyl-2,2-dimethyl-1,3-dioxolane-4-carboxamide (3.49 g, 14.8 mmol) in a 50% aqueous acetic acid solution (86 mL) was heated at reflux (30 min). The solvent was evaporated in vacuo, and the resulting residue was purified by silica gel column chromatography (10% MeOH-$CHCl_3$) to obtain the desired product as a white solid (2.26 g, 78%); mp 83°–84° C.; $R_f$ 0.35 (10% MeOH-$CHCl_3$); $[\alpha]^{23}D=-35.1°$ (c=0.10, MeOH); IR (KBr) 3337, 1649, 1623, 1546, 1109, 1049, 971, 739, 697 $cm^{-1}$; $^1H$ NMR (DMSO-$d_6$) δ 3.45–3.59 (m, CHH'OH), 3.60–3.66 (m, CHH'OH), 3.90–3.98 (m, CHOH), 4.29 (d, J=6.3 Hz, $CH_2Ph$), 4.65–4.85 (m, OH), 5.40–5.65 (m, OH), 7.15–7.40 (m, PhH), 8.25 (t, J=6.0 Hz, NH); $^{13}C$ NMR (DMSO-$d_6$) 41.8 ($CH_2Ph$), 64.1 ($CH_2OH$), 73.2 (CHOH), 126.7 ($C_4'$), 127.2 ($2C_2'$ or $2C_3'$), 128.3 ($2C_2'$ or $2C_3'$), 139.7 ($C_1'$) 172.4 (C(O)NH) ppm; MS (+Cl) 196 ($M^+$+1); $M_r$(+Cl) 196.097 09 [$M^+$+1] (calcd. for $C_{10}H_{14}NO_3$ 196.097 37); Anal ($C_{10}H_{13}NO_3$) C, H, N.

D. (S)-N-Benzyl-2,3-dimethoxypropionamide.

To an acetonitrile solution (74 mL) of (S)-N-benzyl-2,3-dihydroxptopionamide (2.26 g, 11.6 mmol), was added $Ag_2O$ (13.40 g, 58 mmol) and methyl iodide (7.4 mL, 116 mmol), and the resulting mixture was stirred at room temperature for 2 days. The salts were filtered, and the filtrate was evaporated in vacuo to obtain a clear oil which was purified by silica gel column chromatography (EtOAc) to give the above-identified product (1.89 g, 70%) as a clear oil; $R_f$ 0.43 (EtOAc); $[\alpha]^{23}D=-33.2°$ (c=0.07, MeOH); IR (liquid film) 3324, 2931, 1667, 1528, 1455, 1108, 701 $cm^{-1}$; $^1H$ NMR ($CDCl_3$) δ 3.41 (s, $CH_2OCH_3$), 3.49 (s, $CHOCH_3$), 3.72 (dd, J=4.5, 10.5 Hz, CHH'$OCH_3$), 3.80 (dd, J=27, 10.5 Hz, CHH'$OCH_3$), 3.88 (dd, J=2.7, 4.5Hz, $CHOCH_3$), 4.51 (d, J=6.0 Hz, $CH_2Ph$), 6.85–7.03 (m, NH), 7.25–7.38 (m, PhH), addition of excess (R)-mandelic acid gave only one signal for the $CH_2OCH_3$ protons; $^{13}C$ NMR ($CDCl_3$) 42.8 ($CH_2Ph$), 58.5 ($CH_2OCH_3$), 59.2 ($CHOCH_3$) 72.2 ($CH_2OCH_3$), 81.7 ($CHOCH_3$), 127.3 ($C_4'$), 127.5 ($2C_2'$ or $2C_3'$), 128.5 ($2C_2'$ or $2C_3'$), 138.0 ($C_1'$), 169.9 (C(O)NH) ppm; MS (+Cl) (rel. intensity) 224 ($M^+$+1, 100), 222(11), 191(2); $M_r$(+Cl) 224.129 29 [$M^+$+1] (calcd. for $C_{12}H_{18}NO_3$ 224.128 67); Anal ($C_{12}H_{17}NO_3$Ω0.25 $H_2O$) C,H,N.

EXAMPLE 3

(R)-N-Benzyl-2,3-dimethoxypropionamide

A. Potassium (R)-2,2-dimethyl-1,3-dioxolane-4-carboxylate.

A solution of (S)-(+)-2,2-dimethyl-1,3-dioxolane-4-methanol (2.00 g, 15 mmol) and KOH (0.90 g, 16 mmol) in $H_2O$ (60 mL) was cooled to 0° and $KMnO_4$ (2.52 g, 16 mmol) was incrementally added. Upon addition, the reaction mixture was allowed to warm to room temperature and then stirred for additional 2 hours. The mixture was filtered through Celite and the clear filtrate was adjusted to pH 8.0 with 5% aqueous $H_2SO_4$. The resulting solution was evaporated in vacuo, and the white residue was suspended in boiling EtOH (100 mL) and filtered. Evaporation of the solvent gave the desired product (2.00 g, 72%) as a white solid: $[\alpha]^{23}D=+29.5°$ (c=0.4, $H_2O$) (lit. $[\alpha]^{23}D=+30.1°$ (c=1.03, $H_2O$)).

B. (R)-N-Benzyl-2,2-dimethyl-1,3-dioxolane-4-carboxamide.

Potassium (R)-2,2-dimethyl-1,3-dioxolane-4-carboxylate (1.31 g, 7.1 mmol) was suspended in dry $CH_2Cl_2$ (50 mL) under $N_2$ and then trifluoroacetic acid (0.81 g, 7.1 mmol) was added and the reaction stirred at room temperature (30 min). 1,1'-Carbonyldiimidazole (1.15 g, 7.1 mmol) was then introduced at room temperature, and the reaction was heated at reflux until $CO_2$ evolution ceased. The reaction mixture was cooled to room temperature, benzylamine (0.78 mL, 7.1 mmol) was added and the reaction stirred (18 hours). The $CH_2Cl_2$ suspension was washed with water (2×25 mL), and the organic layer separated, dried ($Na_2S_2O_4$), and evaporated in vacuo. The residue was purified by silica gel column chromatography (5% MeOH-$CHCl_3$) to obtain the crude amide, which was further purified by recrystallization from ethyl ether-petroleum ether to give the pure amide (1.22 g, 73%; $R_f$ 0.70 (5% MeOH-$CHCl_3$; mp 81°–84° C.; $[\alpha]^{23}D=$ +17.1° (c=0.08, MeOH); IR (KBr) 3336, 1649, 1540, 1221, 1090, 735, 500 $cm^1$; $^1H$ NMR ($CDCl_3$) δ 1.39 (s, $CCH_3$), 1.45 (s, $CCH_3$), 4.16 (dd, J=5.4, 9.0 Hz, OCHH'), 4.32 (dd, J=7.4, 9.0 Hz, OCHH'), 4.49 (d, J=6.0 Hz, $CH_2Ph$), 4.55 (dd, J=5.4, 7.4 Hz, OCH), 6.80–6.95 (m, NH), 7.23–7.41 (m, PhH); $^{13}C$ NMR ($CDCl_3$) 25.1 ($CCH_3$), 26.3 ($CCH_3$) 43.0 ($CH_2Ph$), 67.9 ($CH_2$), 75.2 (CH) 111.0 ($C(CH_3)_2$), 127.7 ($2C_2'$ or $2C_3'$ and $C_4'$), 128.9 ($2C_2'$ or $2C_3'$), 137.9 ($C_1'$), 171.3 (C(O)) ppm; MS(+Cl) (rel. intensity) 236 (M$^+$+1, 100), 208(72), 178 (43); M$_r$ (+Cl) 236.128 99 [M$^+$+1] (calcd. for $C_{13}H_{18}NO_3$); Anal ($C_{13}H_{17}NO_3$·0.5 $H_2O$) C,H, N.

C. (R)-N-Benzyl-2,3-dihydroxypropionamide.

A 50% aqueous acetic acid solution (30 mL) containing (R)-N-benzyl-2,2-dimethyl-1,3-dioxolane-4-carboxamide (1.22 g, 5.19 mmol) was heated at reflux (30 min). The solvents were evaporated in vacuo and the resulting residue was purified by silica gel column chromatography (10% MeOH-CHCl$_3$) to obtain the desired product as a white solid (0.86 g, 85%); mp 83°–84° C., R$_f$ 0.35 (10% MeOH-CHCl$_3$); $[\alpha]^{23}D=+35.4°$ (c=0.19, MeOH); IR (KBr) 3336, 1649, 1623, 1542, 1400, 1319, 1110, 1049, 972, 739, 697 cm$^{-1}$; $^1$H NMR (DMSO-d$_6$) δ 3.42–3.55 (m, CHH'OH), 3.53–3.64 (m, CHH'OH), 3.89–3.95 (m, CHOH), 4.28 (d, J=6.0 Hz, CH$_2$Ph), 4.74 (t, J=5.7 Hz, CH$_2$OH), 5.57 (d, J=5.4Hz, CHOH) 7.19–7.35 (m, PhH), 8.24 (t, J=6.0 Hz, NH); 13C NMR (DMSO-d$_6$) 41.7 (CH$_2$Ph), 64.0 (CH$_2$OH), 73.1 (CHOH), 126.6 (C$_4$'), 127.2 (2C$_2$' or 2C$_3$'), 128.2 (2C$_2$' or 2C$_3$'), 139.6 (C$_1$'), 172.2 (C(O)NH) ppm; MS(+Cl) (rel. intensity) 196 (M$^+$+1, 100); M$_r$ (+Cl) 196.098 03 [M$^+$+1] (calcd. for $C_{10}H_{14}NO_3$ 196.097 37); Anal. ($C_{10}H_{13}NO_3$) C, H, N.

D. (R)-N-Benzyl-2,3-dimethoxypropionamide

To an acetonitrile solution (44 mL) of (R)-N-benzyl-2,3-dihydroxypropionamide (1.35 g, 6.94 mmol) was added Ag$_2$O (8.05 g, 35 mmol) and methyl iodide (4.4 mL, 70 mmol), and then the mixture was stirred at room temperature (2 days). The salts were filtered, and the filtrate was evaporated in vacuo to obtain a clear oil which was purified by silica gel column chromatography (EtOAc) to give (R)-N-benzyl-2,3-dimethoxypropionamide (1.29 g, 83%) as a clear oil: R$_f$ 0.43 (EtOAc); $[\alpha]^{23}D=+33.6°$ (c=0.10 MeOH); IR (liq. film) 3320, 2930, 1662, 1528, 1455, 1107, 700 cm$^{-1}$; $^1$H NMR (CDCl$_3$) δ 3.41 (s, CH$_2$OCH$_3$), 3.71 (dd, J=4.5, 10.5 Hz, CHH'OCH$_3$), 3.80 (dd, J=2.7, 10.5 Hz, CHH'OCH$_3$), 3.88 (dd, J=2.7, 4.5 Hz, CHOCH$_3$), 4.51 (d, J=6.0 Hz, PhCH$_2$), 6.95–7.05 (m, NH), 7.28–7.40 (m, PhH), addition of excess (R)-mandelic acid gave only one signal for the CH$_2$OCH$_3$ protons; $^{13}$C NMR (CDCl$_3$) 43.0 (CH$_2$Ph), 58.6 (CH$_2$OCH$_3$), 59.4 (CHOCH$_3$), 72.3 (CH$_2$OCH$_3$), 81.8 (CH), 127.5 (C$_4$'), 127.6 (2C$_2$' or 2C$_3$'), 128.7 (2C$_2$' or 2C$_3$'), 138.0 (C$_1$'), 170.0 (C (O) ppm; MS (+Cl) rel. intensity) 224 (M$^+$+1, 100), 119 (3); M$_r$ (+Cl) 224.127 99 [M$^+$+1] (calcd. for $C_{12}H_{18}NO_3$ 224.128 67); Anal. ($C_{12}H_{17}NO_3$·0.15 $H_2O$) C, H, N.

PHARMACOLOGY

Compounds were screened under the auspices of the National Institutes of Health for anticonvulsant activity in male albino Cartworth Farms No. 1 mice (ip route). Activity was established using the electrical (maximal electroshock or MES) test. In the MES test, a drop of electrolyte solution with anesthetic (0.5% butacaine hemisulfate in 0.9% sodium chloride) was used in the eyes of the animals prior to positioning the corneal electrodes and delivery of current. A 60 cycle alternating current was administered for 0.2 sec. at 50 mA. Protection endpoints were defined as the abolition of the hind limb tonic extensor component of the induced seizure. In mice, the effects of compounds on forced spontaneous motor activity were determined using the rotorod test. The inability of animals to maintain their balance for 1 min. on a 1 inch diameter knurled rod at 6 rpms in 3 successive trials demonstrated motor impairment. Normally under these conditions, a mouse can maintain its balance almost indefinitely. In the mouse identification screening study all compounds were given at three dose levels (30, 100, 300 mg/kg) and two time periods (0.5, 4h). Typically, in the MES seizures test one animal was used at 30 mg/kg and 300 mg/kg, and three animals at 100 mg/kg. In the rotorod toxicity test four animals were used at 30 mg/kg, and 300 mg/kg, and eight animals at 100 mg/kg. If activity was found at 30 mg/kg, then lower dosages were used to find the ED$_{50}$ values.

The quantitative determination of the median effective (ED$_{50}$) and toxic doses (TD$_{50}$) were conducted at previously calculated times of peak effect. Groups of at least eight animals were tested using different doses of test compound until at least two points were determined between 100 and 0% protection and minimal motor impairment. The dose of candidate substance required to produce the defined endpoint in 50% of the animals in each test and the 95% confidence interval were calculated.

The results of the compound of the example of the present invention was compared with N-Benzyl-2,3-dihydroxypropimamide and known anticonvulsants under the aforementioned tests, and the results are given in the table hereinbelow.

TABLE 1

Pharmacological Data in Mice[a]

| Stereo-isomer | X | Y | mp[b] | MES[c]ED$_{50}$ | Tox[d]TD$_{50}$ | P.I.[e] |
|---|---|---|---|---|---|---|
| R, S | OCH$_3$ | CH$_2$OCH$_3$ | oil | 30 [0.25] (17–43) | 280 [0.25] (240–300) | 9.3 |
| R, S | OH | CH$_2$OH | 83–84 | >100, <300 [0.5] | >300 | — |
| R | OCH$_3$ | CH$_2$OCH$_3$ | oil | >30, <100 [0.5] | 300 [0.5] | — |
| S | OCH$_3$ | CH$_2$OCH$_3$ | oil | >30, <100 [0.5] | Not reported | — |
| phenytoin | | | | 6.5 [2] (5.7–7.2) | 43 [0.5] (36–48) | 6.6 |
| phenobarbital | | | | 22 [1] (15–23) | 69 [0.5] (63–73) | 3.1 |
| valproate | | | | 290 [0.25] (240–360) | 480 [0.25] (410–570) | 1.7 |

[a]The compounds were administered intraperitoneally. ED$_{50}$ and TD$_{50}$ values are in mg/kg. Numbers in parentheses are 95% confidence intervals. A dose effect data for these compounds was obtained at the *time of peak effect* (indicated in hours in the brackets). The compounds were tested through the auspices of the National Institute of Neurological and Communicative Disorders and Stroke at the National Institutes of Health.
[b]Melting points (°C.) are uncorrected.
[c]MES = maximal electroshock seizure test.
[d]Neurologic toxicity determined using the rotorod test unless otherwise noted.
[e]PI = protective index (TD$_{50}$/ED$_{50}$).

The results clearly show that the dihydroxy compound has very low anticonvulsant activity. On the other hand, the compounds of the present invention, e.g., N-Benzyl 2,3-Dimethoxypropionamide have much greater efficacy. In fact, the ED$_{50}$ of the diether of the present invention is greater than 3 times more effective than that of the dihydroxy compound. Moreover, the P.I. of the diether of the present invention is greater than 3 times more effective than that of the dihydroxy compound.

The data also illustrate that compounds of the present invention, such as N-Benzyl 2,3-dimethyoxypropionamide, exhibit excellent drug profiles, as indicated by its unexpectedly high protective index. The protective index measures the relationship between the doses of a drug required to produce undesired and desired effects, respectively, and is measured as the ratio between the median toxic dose and the median effective dose ($TD_{50}/ED_{50}$). As shown by the data, the diether has a P.I. of 9.3, which is significantly greater than the P.I. values of phenytoin, phenobarbital and valproate. Thus, the data clearly indicate that compounds of the present invention are excellent anticonvulsant drugs.

The above preferred embodiments and examples are given to illustrate the scope and spirit of the present invention. The embodiments and examples described herein will make apparent to those skilled in the art other embodiments and examples. These other embodiments and examples are within the contemplation of the present invention. Therefore, the present invention should be limited only by the appended claims.

What is claimed:

1. A compound of the formula:

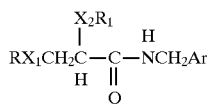

or pharmaceutically acceptable salts thereof wherein

Ar is aryl which is unsubstituted or substituted with at least one electron donating group or electron withdrawing group;

R and $R_1$ are independently lower alkyl, aryl, aryl lower alkyl, lower cycloalkyl or lower cycloalkyl lower alkyl, wherein R and $R_1$ groups are independently unsubstituted or substituted with at least one electron donating group or electron withdrawing group;

$X_1$ and $X_2$ are independently O, S, or $NR_3$ and $R_3$ is hydrogen or lower alkyl.

2. The compound according to claim 1 wherein R and $R_1$ are the same.

3. The compound according to claim 1 wherein $X_1$ and $X_2$ are the same.

4. The compound according to claim 1 wherein $X_1$ and $X_2$ are the same and $R_1$ and R are the same.

5. The compound according to claim 1 wherein $X_1$ and $X_2$ are independently O, S, NH or $NCH_3$.

6. The compound according to claim 5 wherein $X_1$ and $X_2$ are independently O or S.

7. The compound according to claim 6 wherein $X_1$ and $X_2$ are the same.

8. The compound according to claim 6 wherein $X_1$ and $X_2$ are O.

9. The compound according to claim 1 wherein R and $R_1$ are independently lower alkyl.

10. The compound according to claim 1 wherein R and $R_1$ are independently alkyl containing 1–3 carbon atoms.

11. The compound according to claim 10 wherein R and $R_1$ and methyl.

12. The compound according to claim 1 having the formula:

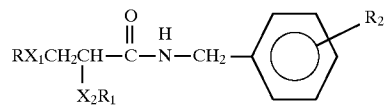

wherein

R and $R_1$ are independently lower alkyl, aryl, aryl lower alkyl, cycloalkyl or cycloalkyl lower alkyl, said R and $R_1$ groups being unsubstituted or substituted with an electron donating group or electron withdrawing group;

$X_1$ and $X_2$ are independently O, S, or $NR_3$;

$R_3$ is hydrogen or lower alkyl; and $R_2$ is hydrogen, an electron donating group or an electron withdrawing group.

13. The compound according to claim 12 wherein $X_1$ and $X_2$ are independently O, S, NH or $NCH_3$.

14. The compound according to claim 13 wherein R and $R_1$ are independently lower alkyl.

15. The compound according to claim 12 wherein $X_1$ and $X_2$ are the same.

16. The compound according to claim 13 wherein $X_1$ and $X_2$ are independently O or S.

17. The compound according to claim 16 wherein $X_1$ and $X_2$ are both S or are both O.

18. The compound according to claim 12 wherein R and $R_1$ are independently alkyl containing 1–3 carbon atoms.

19. The compound according to claim 14 or 18 wherein R and $R_1$ are the same.

20. The compound according to claim 12 of the formula

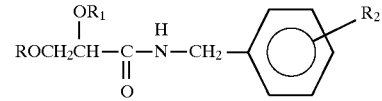

21. The compound according to claim 20 wherein R and $R_1$ are independently lower alkyl.

22. The compound according to claim 21 wherein R and $R_1$ are independently lower alkyl containing 1–3 carbon atoms.

23. The compound according to claim 22 wherein $R_1$ and R are the same.

24. The compound according to claim 20 which is N-Benzyl 2,3-dimethoxypropionamide.

25. A stereoisomer of the compound of claim 1.

26. A stereoisomer of the compound of claim 12.

27. A stereoisomer of the compound of claim 20.

28. A stereoisomer of the compound of claim 24.

29. A pharmaceutical composition comprising an anticonvulsant effective amount of a compound according to any one of claims 1, 12, 20 or 24 and a pharmaceutical carrier therefor.

30. A method of treating central nervous system disorders in an animal in need of such treatment comprising administering to said animal an anticonvulsant effective amount of a compound according to any one of claims 1, 12, 20 or 24.

31. The method according to claim 30 wherein said animal is a mammal.

32. The method according to claim 31 wherein said mammal is human.

33. The method according to claim 30 wherein the compound is administered in an amount ranging from about 0.5 to about 100 mg/kg of body weight per day.

* * * * *

UNITED STATES PATENT AND TRADEMARK OFFICE
CERTIFICATE OF CORRECTION

PATENT NO. : 5,880,158
DATED : March 9, 1999
INVENTOR(S) : Harold Kohn

Page 1 of 1

It is certified that error appears in the above-identified patent and that said Letters Patent is hereby corrected as shown below:

Title page,
Item [21], Appl. No. "938,527" should read -- 08/938,527 --

Column 14,
Example 1, line 9, "C.." should read -- C, --

Column 15,
Line 36, "$CHC_3$" should read -- $CHCl_3$ --

Column 16,
Line 3, "dihydroxyptopionamide" should read -- dihydroxypropionamide --
Line 24, "$(C_{12}H_{17}NO_3\Omega 0.25\ H_2O)$" should read -- $(C_{12}H_{17}NO_3 \bullet 0.25\ H_2O)$ --

Column 17,
Line 4, "$(C_{13}H_{17}NO_3\Omega 0.5\ H_2O)$" should read -- $(C_{13}H_{17}NO_3 \bullet 0.5\ H_2O)$ --
Line 46, "$(C_{12}H_{17}NO_3\Omega 0.15\ H_2O)$" should read -- $(C_{12}H_{17}NO_3 \bullet 0.15\ H_2O)$ --

Signed and Sealed this

Seventh Day of May, 2002

*Attest:*

*Attesting Officer*

JAMES E. ROGAN
*Director of the United States Patent and Trademark Office*